US007230109B2

(12) United States Patent
Sasse et al.

(10) Patent No.: US 7,230,109 B2
(45) Date of Patent: Jun. 12, 2007

(54) 5-[4-[2-(N-METHYL-N-(2-PYRIDYL)AMINO) ETHOXY]BENZYL]THIAZOLIDINE-2, 4-DIONE, MALEIC ACID SALT, HYDRATE AS PHARMACEUTICAL

(75) Inventors: Michael John Sasse, Tunbridge Wells (GB); Paul David James Blackler, Tonbridge (GB); David C Lee, Linton (GB)

(73) Assignee: SmithKline Beecham p.l.c., Brentford, Middlesex (GB)

( * ) Notice: Subject to any disclaimer, the term of this patent is extended or adjusted under 35 U.S.C. 154(b) by 0 days.

(21) Appl. No.: 10/849,591

(22) Filed: May 20, 2004

(65) Prior Publication Data
US 2004/0214865 A1 Oct. 28, 2004

Related U.S. Application Data

(63) Continuation of application No. 10/321,055, filed on Dec. 17, 2002, which is a continuation of application No. 10/082,879, filed on Feb. 26, 2002, now abandoned, which is a continuation of application No. 09/581,826, filed as application No. PCT/EP98/08155 on Dec. 14, 1998, now abandoned.

(30) Foreign Application Priority Data
Dec. 16, 1997 (GB) .................... 9726566.4

(51) Int. Cl.
C07D 417/12 (2006.01)
A61K 31/44 (2006.01)
(52) U.S. Cl. .................... 546/269.7; 514/342
(58) Field of Classification Search ............ 546/268.1, 546/269.7; 514/336, 342
See application file for complete search history.

(56) References Cited

U.S. PATENT DOCUMENTS

| 5,002,953 | A | 3/1991 | Hindley et al. |
| 5,741,803 | A | 4/1998 | Pool et al. .................... 514/342 |
| 5,910,592 | A | 6/1999 | Pool et al. ................. 546/269.7 |
| 6,288,095 | B1 | 9/2001 | Hindley et al. ............. 514/367 |
| 6,664,278 | B2 | 12/2003 | Sasse et al. .................. 514/342 |
| 6,806,280 | B1 | 10/2004 | Blackler et al. ............ 514/342 |
| 6,815,457 | B1 | 11/2004 | Blackler et al. ............ 514/342 |
| 2002/0099081 | A1 | 7/2002 | Blackler et al. |
| 2002/0133016 | A1 | 9/2002 | Lynch et al. |

FOREIGN PATENT DOCUMENTS

| EP | 0 306 228 | 8/1989 |
| EP | 1 468 997 | 10/2004 |
| WO | WO 93/10254 | 5/1993 |
| WO | 94/05659 | * 3/1994 |
| WO | WO 94/05669 | 3/1994 |
| WO | WO 95/21603 | 8/1995 |
| WO | WO 95/21608 | 8/1995 |
| WO | WO 94/05659 | 3/1999 |
| WO | WO 99/31093 | 6/1999 |
| WO | WO 00/64892 | 11/2000 |
| WO | WO 00/64893 | 11/2000 |
| WO | WO 00/64896 | 11/2000 |
| WO | WO 02/26737 | 4/2002 |
| WO | WO 04/085435 | 10/2004 |
| WO | WO 05/021541 | 3/2005 |

OTHER PUBLICATIONS

Phadnis et al., "Identfication of drugs in pharmaceutical dosage from by X-ray powder diffrectometry", *J. Pharm. Biomed. Analysis*, 15: 929-943 (1997).
Chakravarty et al., "Crystal forms of tolbutamide from acetonitrile and 1-octanol:effect of solvent, humidity and compression pressure". *Int. J. Pharmaceutics*, 288: 335-348 (2005).
Muzaffar et al., "Polymorphism and drug availability". *J. Pharmacy(Lahore)*, 1(1): 59-66 (1979).
Jain et al., "Polymorphism in pharmacy". *Indian Drugs*, 23(6): 315-329 (1986).
Taday et al., "Using terahertz plus spectroscopy to study the crystalline structure of a drug: A case study of the polymorphs of ranitidine hydrochloride", *J. Pharm. Sci.*, 92(4): 831-838 (2003).
Otsuka et al., "Effect of polymorphic forms of bulk powders on pharmaceutical properties of carbamazepine granules", *Chem. Pharm. Bull.*, 47(6): 852-856 (1999).
E. Doelker. "Séance thermatique. Modification crystallines et transformations polymorphs au cours des operations galeniques". *Ann. Pharm. Fr.*, 60: 161-176 (2002).
Brittain et al., "Polymorphism in pharmaceutical solids". NY: Marcel Dekker, Inc., 1999, pp. 125-181, 183-226, 228-330 and 331-361.
Office Action: U.S. Appl. No. 09/581,816, Dec. 4, 2000.
Office Action: U.S. Appl. No. 09/581,816, Aug. 10, 2001.
Office Action: U.S. Appl. No. 10/071,339, Jul. 30, 2002.
Office Action: U.S. Appl. No. 10/354,365, Feb. 17, 2005.
Office Action: U.S. Appl. No. 09/581,719, Mar. 30, 2001.
Office Action: U.S. Appl. No. 10/072,096, Mar. 5, 2003.
Office Action: U.S. Appl. No. 10/030,323, Mar. 5, 2003.

(Continued)

*Primary Examiner*—Rita Desai
(74) *Attorney, Agent, or Firm*—Kathryn L. Sieburth; Mary E. McCarthy; Charles M. Kinzig

(57) ABSTRACT

A hydrate of 5-[4-[2-(N-methyl-N-(2-pyridyl)amino) ethoxy]benzyl]thiazolidine-2,4-dione, maleic acid salt, characterized in that it: (i) comprises water in the range of from 0.4 to 2.5% w/w; and (ii) provides an infra red spectrum containing peaks at 1749, 1703, 1645, 1623, 1365 and 736 cm$^{-1}$; and/or (iii) provides an X-ray powder diffraction (XRPD) pattern substantially as set out in FIG. II and/or (iv) provides a Raman spectrum containing peaks at 3106, 3069, 3002, 2961, 1750, 1718, 1684, 1385, 1335, 1229, 1078, 917, 428 and 349 cm$^{-1}$ and/or (iv) provides a solid-state nuclear magnetic resonance spectrum containing chemical shifts substantially as set out in Table I; a process for the preparation of such a compound, a pharmaceutical composition containing such a compound and the use of such a compound or composition in medicine.

12 Claims, 4 Drawing Sheets

OTHER PUBLICATIONS

Figure 1:
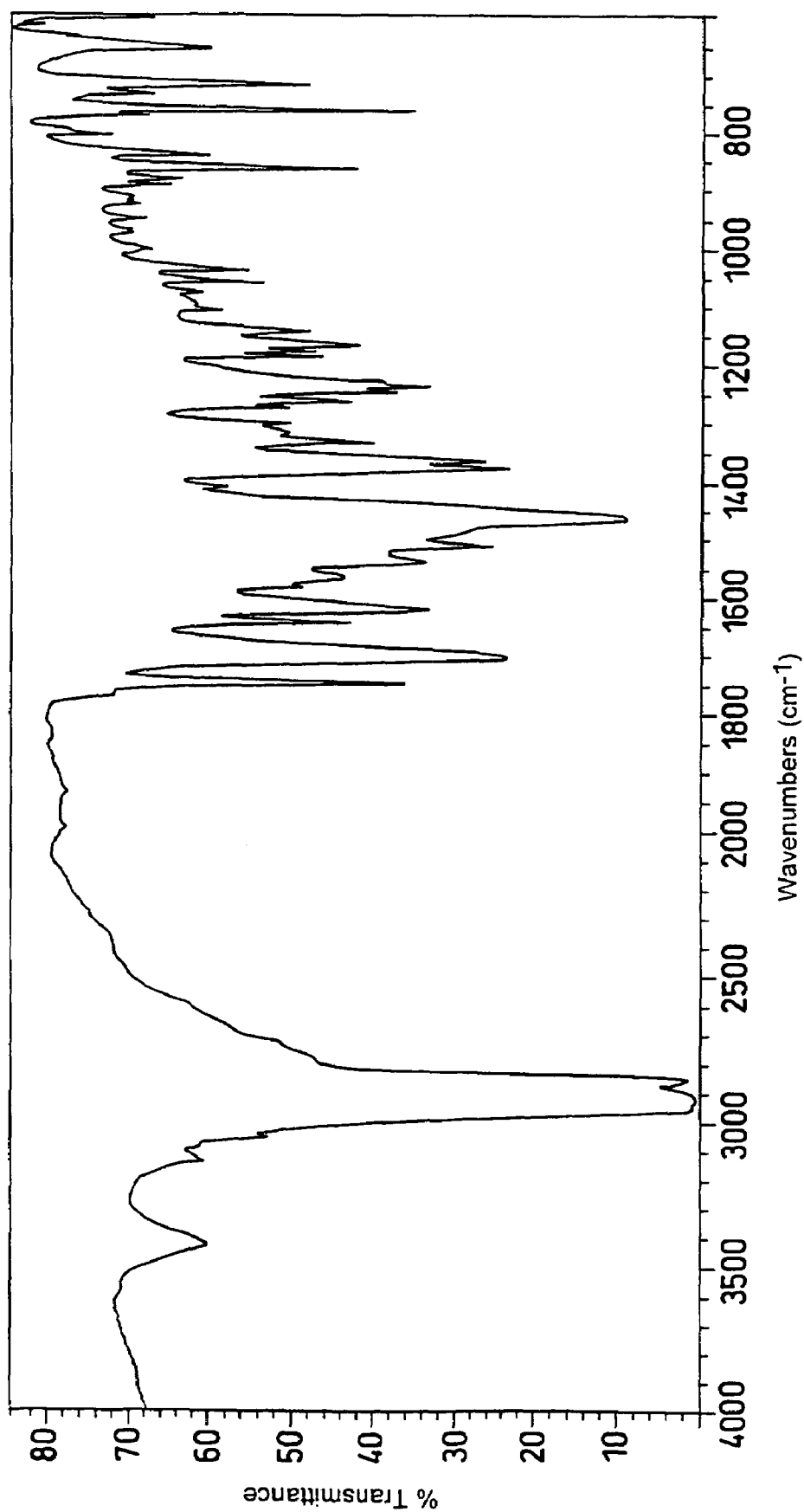

Office Action: U.S. Appl. No. 10/048,123, Jun. 3, 2003.
Office Action: U.S. Appl. No. 10/048,123, Oct. 3, 2003.
Office Action: U.S. Appl. No. 10/030,877, Jul. 11, 2003.
Office Action: U.S. Appl. No. 10/030,877, Nov. 12, 2003.
Office Action: U.S. Appl. No. 10/843,741, Apr. 26, 2005.
Chemical & Engineering News, pp. 32-35 (Feb. 2003).
U.S. Pharmacopia, #23, pp. 1834-1844 (1995).
Concise Encyclopedia Chemistry, pp. 872-873 (1993).
Cantello et al., "Facile Biocatalytic Reduction of the Carbon-Carbon Double Bond of 5-Benzylidenethiazolidine-2,4-diones. Synthesis of (+)-5-[4-[2-methyl(2-pyridyl)amino)ethoxy]benzyl]thiazolidine-2,4-dione (BRL 49653), its (R)-(+)-Enantiomer and Analogues". *J. Chem. Soc., Perkin Trans. 1*, pp. 3319-3324 (1994).
Cantello et al., "The Synthesis of BRL 49653 — A Novel and Potent Antihyperglycaemic Agent", *Bioorg. & Med. Chem. Lett.*, 4(*10*): 1181-1184 (1994).
Haleblian et al., "Pharmaceutical Applications of Polymorphism". *J. Pharm., Sci.*, 58 (8): 911-929 (1969).
The American Heritage Dictionary of the English Language: Fourth Edition. 2000. http://www.bartleby.com/61/32/10253200.html.

* cited by examiner

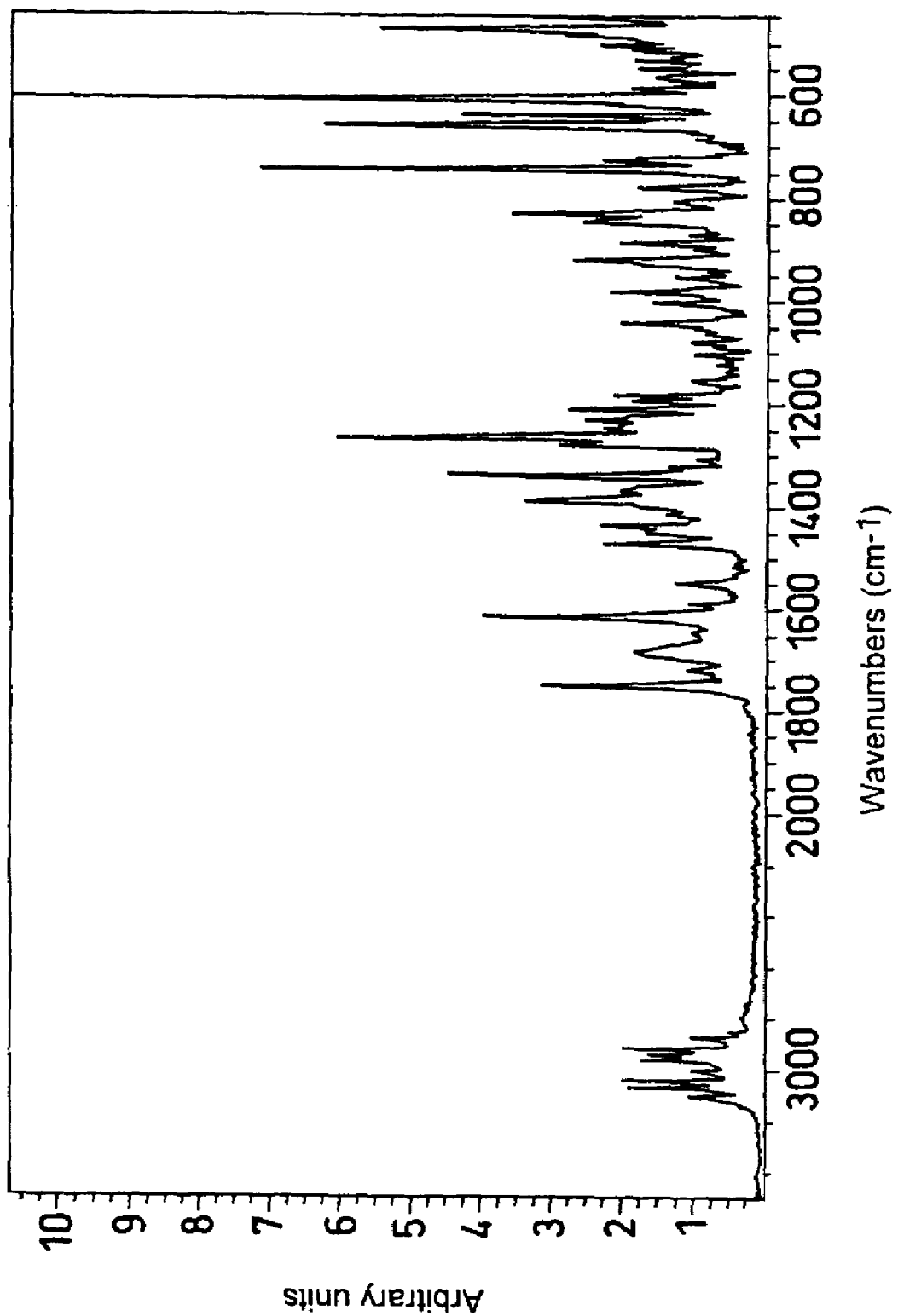
Fig. 3  Raman Spectrum of Hydrate

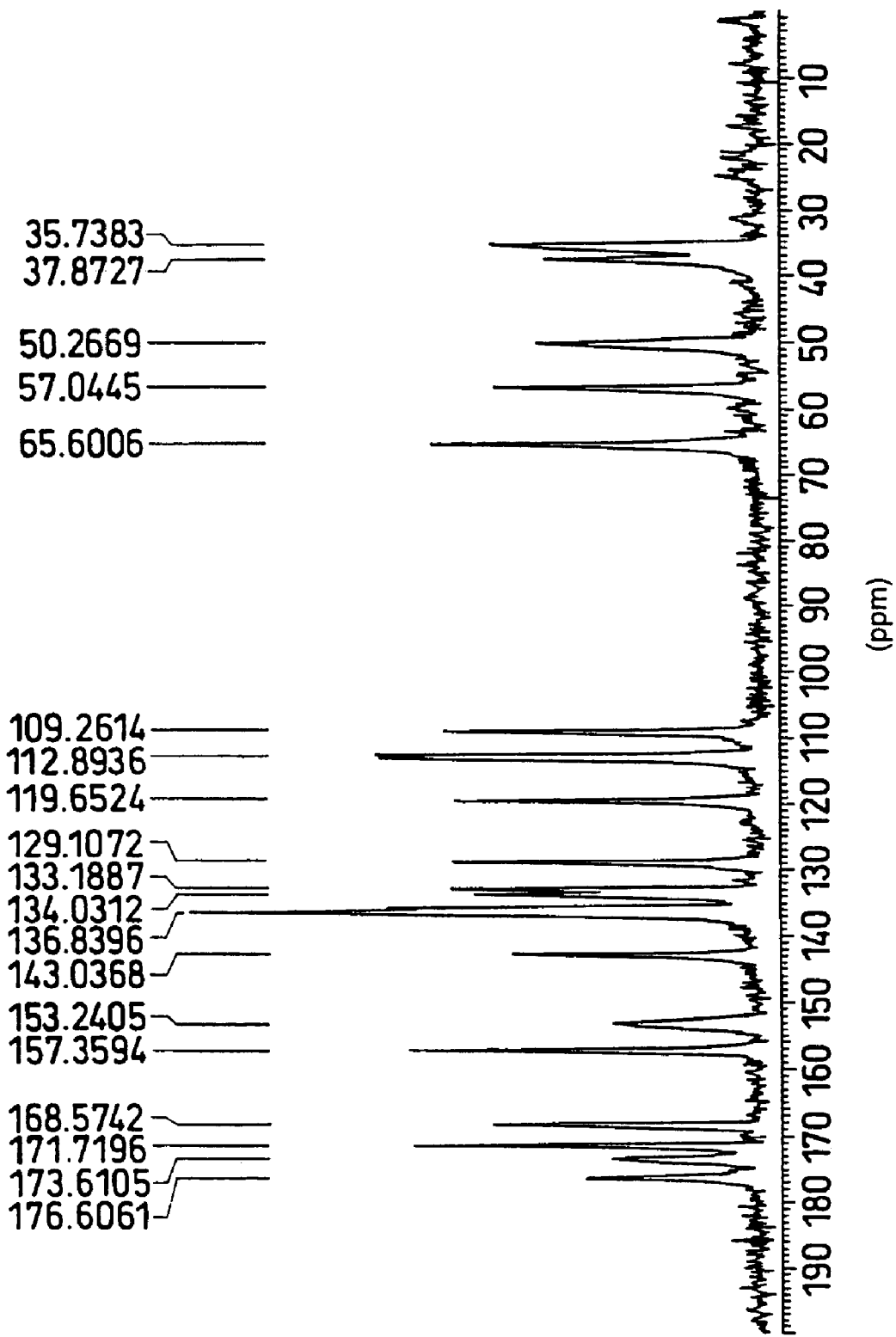
Fig. 4  $^1$H Decoupled $^{13}$C CP-MAS NMR spectrum of the Hydrate

5-[4-[2-(N-METHYL-N-(2-PYRIDYL)AMINO) ETHOXY]BENZYL]THIAZOLIDINE-2, 4-DIONE, MALEIC ACID SALT, HYDRATE AS PHARMACEUTICAL

This application is a continuation of U.S. patent application Ser. No. 10/321,055, filed Dec. 17, 2002, which is a continuation of U.S. patent application Ser. No. 10/082,879, filed Feb. 26, 2002 now abandoned, which is a continuation of U.S. patent application Ser. No. 09/581,826, filed Jun. 16, 2000 now abandoned, which is a 371 of International Application No. PCT/EP98/08155, filed Dec. 14, 1998.

This invention relates to a novel pharmaceutical, to a process for the preparation of the pharmaceutical and to the use of the pharmaceutical in medicine.

International Patent Application, Publication Number WO94/05659 discloses certain thiazolidinedione derivatives having hypoglycaemic and hypolipidaemic activity including 5-[4-[2-(N-methyl-N-(2-pyridyl)amino)ethoxy]benzyl] thiazolidine-2,4-dione, maleic acid salt (hereinafter also referred to as "Compound (I)").

Compound (I) is disclosed solely as an anhydrous form. It has now been discovered that Compound (I) exists in a novel form which is particularly suitable for bulk preparation and handling. This can be prepared by an efficient, economic and reproducible process particularly suited to large scale preparation.

The novel form also has useful pharmaceutical properties and in particular it is indicated to be useful for the treatment and/or prophylaxis of diabetes mellitus, conditions associated with diabetes mellitus and certain complications thereof.

Accordingly, the present invention provides a novel form of 5-[4-[2-(N-methyl-N-(2-pyridyl)amino)ethoxy]benzyl] thiazolidine-2,4-dione, maleic acid salt (the "Hydrate") characterised in that the Hydrate:
(i) comprises water in the range of from 0.4 to 2.5% w/w; and
(ii) provides an infra red spectrum containing peaks at 1749, 1703, 1645, 1623, 1365 and 736 cm$^{-1}$; and/or
(iii) provides an X-ray powder diffraction (XRPD) pattern substantially as set out in Table I and /or
(iv) provides a Raman spectrum containing peaks at 3106, 3069, 3002, 2961, 1750, 1718, 1684, 1385, 1335, 1229, 1078, 917, 428 and 349 cm$^{-1}$ and/or
(iv) provides a solid-state nuclear magnetic resonance spectrum containing chemical shifts substantially as set out in Table II.

Suitably the Hydrate contains water in the range of from 0.5 to 2% w/w, such as from 1.5 to 2.0% w/w or from 1.85 to 2.0% w/w, for example 1.85, 1.86, 1.87 or 1.88% w/w.

In one favoured aspect, the Hydrate provides an infra red spectrum substantially in accordance with FIG. 1.

Figure 2:
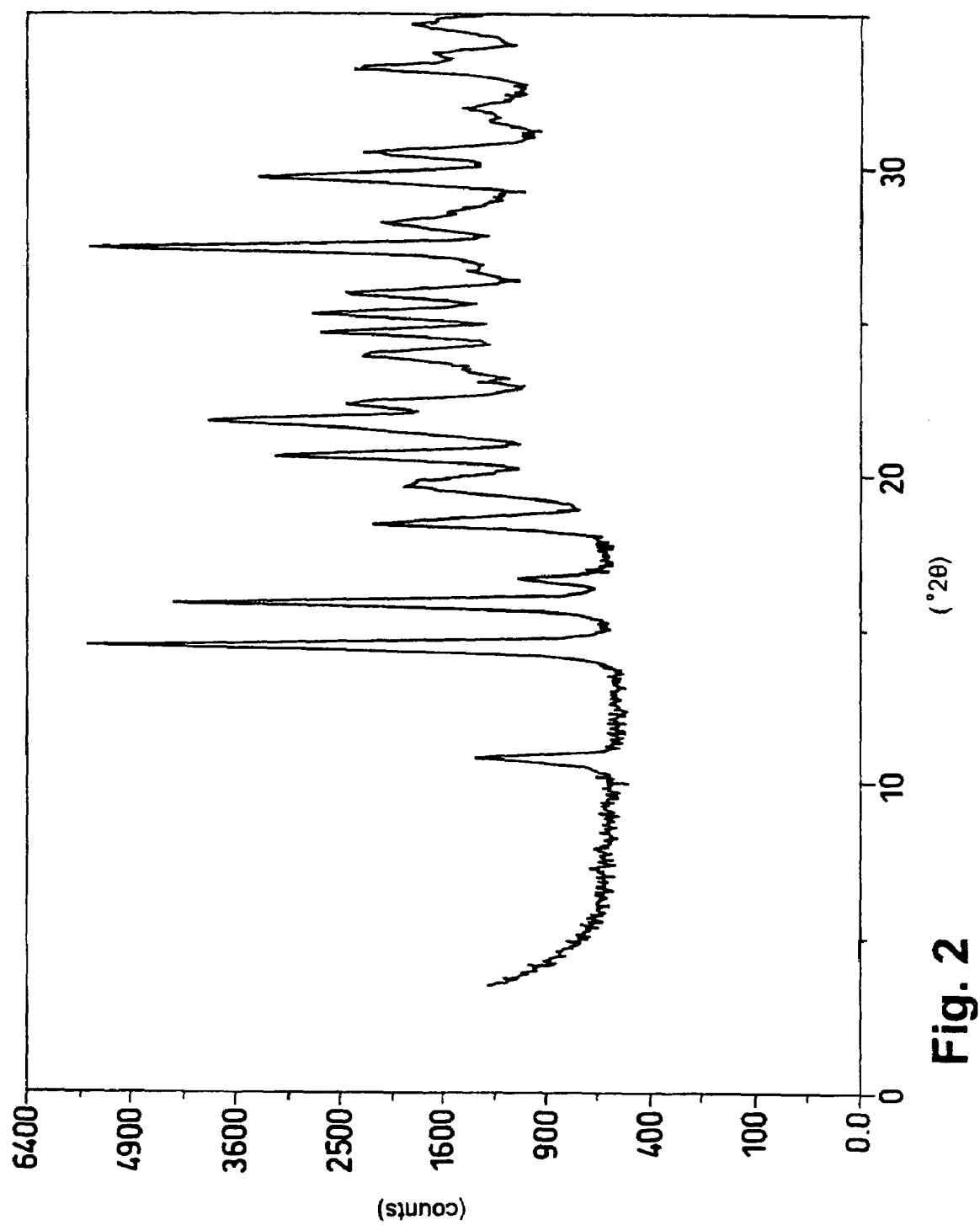

In one favoured aspect, the Hydrate provides an X-ray powder diffraction (XRPD) pattern substantially in accordance with FIG. 2.

In a further favoured aspect, the Hydrate provides a Raman spectrum substantially in accordance with FIG. 3.

In yet a further favoured aspect, the Hydrate provides a solid-state nuclear magnetic resonance infra red spectrum substantially in accordance with FIG. 4.

The present invention encompasses the Hydrate isolated in pure form or when admixed with other materials, for example the known anhydrous form of Compound I, the above mentioned reversibly rehydratable forms or any other material.

Thus in one aspect there is provided the Hydrate in isolated form.

In a further aspect there is provided the Hydrate in pure form.

In yet a further aspect there is provided the Hydrate in crystalline form.

The invention also provides a process for preparing the Hydrate, characterised in that 5-[4-[2-(N-methyl-N-(2-pyridyl)amino)ethoxy]benzyl]thiazolidine-2,4-dione, maleic acid salt is crystallised from ethanol, suitably denatured ethanol, containing 15 to 25% by volume of water, for example 17.5% by volume.

Other aqueous solvents may also be used in the said crystallisation of the Hydrate, for example methanol, acetonitrile or ethyl acetate or mixtures thereof. The precise amount of water used in each of the alternative solvents will depend upon the particular solvent chosen, for example approximately 3% by volume in acetonitrile or ethyl acetate. Methanol has also been shown to provide the hydrate when the crystallisation is conducted open to the atmosphere. Water can also be used as the crystallization solvent.

Compound I is prepared according to known procedures, such as those disclosed in WO94/05659. The disclosures of WO94/05659 are incorporated herein by reference.

When used herein the term 'prophylaxis of conditions associated with diabetes mellitus' includes the treatment of conditions such as insulin resistance, impaired glucose tolerance, hyperinsulinaemia and gestational diabetes.

Diabetes mellitus preferably means Type II diabetes mellitus.

Conditions associated with diabetes include hyperglycaemia and insulin resistance, especially acquired insulin resistance and obesity. Further conditions associated with diabetes include hypertension, cardiovascular disease, especially atherosclerosis, certain eating disorders, in particular the regulation of appetite and food intake in subjects suffering from disorders associated with under-eating, such as anorexia nervosa, and disorders associated with over-eating, such as obesity and anorexia bulimia. Additional conditions associated with diabetes include polycystic ovarian syndrome and steroid induced insulin resistance.

The complications of conditions associated with diabetes mellitus encompassed herein includes renal disease, especially renal disease associated with the development of Type II diabetes including diabetic nephropathy, glomerulonephritis, glomerular sclerosis, nephrotic syndrome, hypertensive nephrosclerosis and end stage renal disease.

As mentioned above the compound of the invention has useful therapeutic properties: The present invention accordingly the Hydrate for use as an active therapeutic substance.

More particularly, the present invention provides the Hydrate for use in the treatment and/or prophylaxis of diabetes mellitus, conditions associated with diabetes mellitus and certain complications thereof.

The Hydrate may be administered per se or, preferably, as a pharmaceutical composition also comprising a pharmaceutically acceptable carrier. The formulation of the Hydrate and dosages thereof are generally as disclosed for Compound (I) in International Patent Application, Publication Number, WO94/05659.

Accordingly, the present invention also provides a pharmaceutical composition comprising the Hydrate and a pharmaceutically acceptable carrier therefor.

The Hydrate is normally administered in unit dosage form.

The active compound may be administered by any suitable route but usually by the oral or parenteral routes. For such use, the compound will normally be employed in the form of a pharmaceutical composition in association with a pharmaceutical carrier, diluent and/or excipient, although the exact form of the composition will naturally depend on the mode of administration.

Compositions are prepared by admixture and are suitably adapted for oral, parenteral or topical administration, and as such may be in the form of tablets, capsules, oral liquid preparations, powders, granules, lozenges, pastilles, reconstitutable powders, injectable and infusable solutions or suspensions, suppositories and transdermal devices. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

Solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the active compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the active compound is suspended in the vehicle instead of being dissolved and sterilised by exposure to ethylene oxide before suspending in the sterile vehicle. Advantageously, a surfactant or wetting agent is included in the composition to facilitate uniform distribution of the active compound.

In addition such compositions may contain further active agents such as anti-hypertensive agents and diuretics.

As is common practice, the compositions will usually be accompanied by written or printed directions for use in the medical treatment concerned.

As used herein the term 'pharmaceutically acceptable' embraces compounds, compositions and ingredients for both human and veterinary use: for example the term 'pharmaceutically acceptable salt' embraces a veterinarily acceptable salt.

The present invention further provides a method for the treatment and/or prophylaxis of diabetes mellitus, conditions associated with diabetes mellitus and certain complications thereof, in a human or non-human mammal which comprises administering an effective, non-toxic, amount of the Hydrate to a human or non-human mammal in need thereof.

Conveniently, the active ingredient may be administered as a pharmaceutical composition hereinbefore defined, and this forms a particular aspect of the present invention.

In the treatment and/or prophylaxis of diabetes mellitus, conditions associated with diabetes mellitus and certain complications thereof the Hydrate may be taken in doses, such as those described above.

Similar dosage regimens are suitable for the treatment and/or prophylaxis of non-human mammals.

In a further aspect the present invention provides the use of the Hydrate for the manufacture of a medicament for the treatment and/or prophylaxis of diabetes mellitus, conditions associated with diabetes mellitus and certain complications thereof.

No adverse toxicological effects are indicated in the above mentioned treatments for the compounds of the invention.

The following examples illustrate the invention but do not limit it in any way.

EXAMPLE 1

Preparation of the Hydrate of 5-[4-[2-(N-methyl-N-(2-pyridyl)amino)ethoxy]benzyl]thiazolidine-2,4-dione, maleic acid salt.

5-[4-[2-(N-methyl-N-(2-pyridyl)amino)ethoxy]benzyl] thiazolidine-2,4-dione free base (6.0 g) and maleic acid salt (2.1 g, 1.05 molar equivalents) were heated in methanol (40 ml) to 55° C. and held at this temperature for 30 minutes during which a solution was obtained. The solution was filtered, re-heated to 55° C., and then cooled to 0–5° C. and stirred for two hours. The product was filtered, and dried at 52° C. in vacuo for 18 hours to give the title compound (6.7 g, 84%). The water content of the product was 0.54% w/w.

The Hydrate of 5-[4-[2-(N-methyl-N-(2-pyridyl) amino)ethoxy]benzyl]thiazolidine-2,4-dione, maleic acid was also prepared by means of the following procedures:

EXAMPLE 2

5-[4-[2-(N-Methyl-N-(2-pyridyl)amino)ethoxy]benzyl] thiazolidine-2,4-dione (1.5 g, 4.2 mmole) and maleic acid (0.525 g @ 97.6% assay, 4.4 mmole, 1.05 mole equivalents) were heated in methanol (15 ml) and the temperature was held at 60° C. The resulting solution was filtered and then cooled to 0° C. with magnetic stirring at which point a thick suspension was formed. The product, 5-[4-[2-(N-Methyl-N-(2-pyridyl)amino)ethoxy]benzyl]thiazolidine-2,4-dione maleate, was isolated, washed with methanol and dried, in vacuo, at 52° C. (Yield 1.4 g, 70.5%). Water content of the product was 2.0%.

EXAMPLE 3

5-[4-[2-(N-methyl-N-(2-pyridyl)amino)ethoxy]benzyl]thiazolidine-2,4-dione free base (6.0 g) and maleic acid (2.1 g, 1.05 molar equivalents) were heated in acetonitrile (60 ml) containing water (2 ml) to 55° C. and held at this temperature for 30 minutes during which time a solution was obtained. The solution was filtered, re-heated to 55° C., and then cooled to 0–5° C. and stirred for two hours. The product was filtered, and dried at 52° C. in vacuo for 18 hours to give the title compound (5.7 g, 72%). The water content of the product was 1.86% w/w.

EXAMPLE 4

The maleate salt of 5-[4-[2-(N-methyl-N-(2-pyridyl)amino)ethoxy]benzyl]thiazolidine-2,4-dione anhydrate (3.0 g) was heated to 80° C. in water (200 ml), then filtered hot and cooled to 20–25° C. with magnetic stirring. The product was filtered, washed with denatured alcohol (20 ml) and dried at 50° C. to give the title compound (1.6 g, 53%), water content 1.87%.

EXAMPLE 5

The maleate salt of 5-[4-[2-(N-methyl-N-(2-pyridyl)amino)ethoxy]benzyl]thiazolidione-2,4-dione anhydrate (2.0 g) was heated to 75° C. in ethyl acetate (100 ml) containing water (3 ml), then filtered hot and cooled with magnetic stirring to 20–25° C. The product was filtered and dried at 50° C. to give the title compound (1.43 g, 72%), water content 1.88%.

EXAMPLE 6

5-[4-[2-(N-methyl-N-(2-pyridyl)amino)ethoxy]benzyl]thiazolidine-2,4-dione free base (6.0 g) and maleic acid (2.1 g, 1.05 molar equivalents) were heated in denatured ethanol (60 ml) containing water (17.5% by volume) to 60° C. and held at this temperature for 30 minutes during which a solution was obtained. The solution was filtered, re-heated to 55° C., and then cooled to 5–10° C. and stirred for four hours. The product was filtered, and dried at 52° C. in vacuo for 18 hours to give the title compound (5.05 g, 62%), water content 1.85%.

Characterising Data: The following characterising data was generated for the Hydrate from example 2:

A Infrared

The infrared absorption spectrum of a mineral oil dispersion of the Novel form was obtained using a Nicolet 710 FT-IR spectrometer at 2 cm$^{-1}$ resolution. Data were digitised at 1 cm$^{-1}$ intervals. The spectrum obtained is shown in FIG. I. Peak positions are: 3428, 3139, 3054, 1749, 1703, 1645, 1623, 1584, 1566, 1539, 1510, 1411, 1365, 1333, 1318, 1302, 1275, 1264, 1247, 1238, 1187, 1178, 1166, 1143, 1109, 1098, 1078, 1060, 1039, 1006, 979, 972, 956, 929, 924, 917, 896, 885, 864, 843, 810, 775, 764, 736, 718, 656, 604, 598, 587, 562 and 542 cm−1

B X-Ray Powder Diffraction (XRPD)

The XRPD pattern of the Novel form is shown below in FIG. II and a summary of the XRPD angles and calculated lattice spacing characteristic of the Novel form is given in Table I.

A PW1710 X-ray powder diffractometer (Cu X-ray source) was used to generate the spectrum using the following acquisition conditions:

| | |
|---|---|
| Tube anode: | Cu |
| Generator tension: | 40 kV |
| Generator current: | 30 mA |
| Start angle: | 3.5° 2θ |
| End angle: | 35.0° 2θ |
| Step size: | 0.02 |
| Time per step: | 4.550 s |

TABLE I

X-Ray Powder Diffraction Angles and Calculated Lattice Spacing Characteristic of the Novel form.

| Diffraction Angle (°2θ) | Lattice Spacing (Angstroms) |
|---|---|
| 10.9 | 8.13 |
| 14.5 | 6.09 |
| 15.9 | 5.56 |
| 16.7 | 5.30 |
| 18.4 | 4.82 |
| 19.7 | 4.50 |
| 20.7 | 4.29 |
| 21.9 | 4.06 |
| 22.3 | 3.98 |
| 23.9 | 3.72 |
| 24.7 | 3.61 |
| 25.3 | 3.52 |
| 25.9 | 3.44 |
| 27.4 | 3.25 |
| 28.2 | 3.16 |
| 29.7 | 3.01 |
| 30.4 | 2.94 |
| 33.1 | 2.70 |

C Raman

A Raman spectrum of the Hydrate was recorded from a sample held in a glass vial using a Perkin-Elmer 2000R FT-Raman spectrometer at 4 cm$^{-1}$ resolution and is shown in FIG. III. Data were digitised at 1 cm$^{-1}$ intervals. Excitation was achieved using a Nd:YAG laser (1064 nm) with a power output of 500 mW. Peak positions are as follows: 3106, 3069, 3042, 3002, 2961, 2939, 2914, 2872, 1750, 1718, 1684, 1645, 1612, 1586, 1546, 1468, 1445, 1434, 1410, 1385, 1364, 1335, 1304, 1277, 1263, 1246, 1229, 1208, 1192, 1181, 1150, 1121, 1100, 1078, 1039, 1000, 980, 953, 917, 896, 883, 864, 843, 827, 805, 777, 742, 724, 657, 637, 607, 561, 540, 525, 497, 467, 452, 428, 400, 349, 317, and 297 cm$^{-1}$.

D NMR

The 90.55 MHz $^{13}$C-CP-MAS NMR spectrum for the Hydrate is shown below in FIG. IV. Chemical shifts are tabulated in Table II. Data were recorded at ambient temperature and 10 kHz spinning frequency, with minimal prior grinding of the sample, using a Bruker AMX360WB spectrometer, with 1.6 ms cross-polarisation and a repetition time of 15 s. Chemical shifts were referenced to the carboxylate signal of a glycine test sample at 176.4 ppm relative to tetramethylsilane and are judged accurate to within +/−0.5 ppm. Peaks were not assigned.

TABLE II

| ¹³C Chemical Shifts of the Hydrate Chemical Shift (ppm) |
| --- |
| 35.7 |
| 37.9 |
| 50.3 |
| 57.0 |
| 65.6 |
| 109.3 |
| 112.9 (2 resonances) |
| 119.7 |
| 129.1 |
| 133.2 |
| 134.0 |
| 136.1 |
| 136.8 |
| 143.0 |
| 153.2 |
| 157.4 |
| 168.6 |
| 171.7 |
| 173.6 |
| 176.6 |

The invention claimed is:

1. A crystalline 5-[4-[2-(N-methyl-N-(2-pyridyl)amino)ethoxy]benzyl]thiazolidine-2,4-dione, maleic acid salt, hydrate wherein said hydrate contains water in the range of from 1.5 to 2.5% w/w and provides at least one of:
   (i) an infra red spectrum containing peaks at 1749, 1703, 1645, 1623, 1365 and 736 cm$^{-1}$;
   (ii) an X-ray powder diffraction pattern substantially as set out in Table I;
   (iii) a Raman spectrum containing peaks at 3106, 3069, 3002, 2961, 1750, 1718, 1684, 1385, 1335, 1229, 1078, 917, 428 and 349 cm$^{-1}$; and
   (iv) a solid-state $^{13}$C nuclear magnetic resonance spectrum containing chemical shifts substantially at 35.7, 37.9, 50.3, 57.0, 65.6, 109.3, 112.9, 112.9, 119.7, 129.1, 133.2, 134.0, 136.1, 136.8, 143.0, 153.2, 157.4, 168.6, 171.7, 173.6, and 176.6 ppm.

2. A crystalline 5-[4-[2-(N-methyl-N-(2-pyridyl)amino)ethoxy]benzyl]thiazolidine-2,4-dione, maleic acid salt, hydrate wherein said hydrate contains water in the range of from 1.5 to 2.5% w/w and said provides each of:
   (i) an infra red spectrum containing peaks at 1749, 1703, 1645, 1623, 1365 and 736 cm$^{-1}$;
   (ii) an X-ray powder diffraction pattern substantially in accordance with FIG. 2;
   (iii) a Raman spectrum containing peaks at 3106, 3069, 3002, 2961, 1750, 1718, 1684, 1385, 1335, 1229, 1078, 917, 428 and 349 cm$^{-1}$; and
   (iv) a solid-state $^{13}$C nuclear magnetic resonance spectrum containing chemical shifts at 35.7, 37.9, 50.3, 57.0, 65.6, 109.3, 112.9, 112.9, 119.7, 129.1, 133.2, 134.0, 136.1, 136.8, 143.0, 153.2, 157.4, 168.6, 171.7, 173.6, and 176.6 ppm.

3. A crystalline 5-[4-[2-(N-methyl-N-(2-pyridyl)amino)ethoxy]benzyl]thiazolidine-2,4-dione, maleic acid salt, hydrate, wherein said hydrate contains water in the range of from 1.5 to 2.5% w/w and said hydrate in a mineral oil dispersion provides an infra red spectrum substantially in accordance with FIG. 1.

4. A crystalline 5-[4-[2-(N-methyl-N-(2-pyridyl)amino)ethoxy]benzyl]thiazolidine-2,4-dione, maleic acid salt, hydrate, wherein said hydrate contains water in the range of from 1.5 to 2.5% w/w and provides an X-ray powder diffraction pattern substantially in accordance with FIG. 2.

5. A crystalline 5-[4-[2-(N-methyl-N-(2-pyridyl)amino)ethoxy]benzyl]thiazolidine-2,4-dione, maleic acid salt, hydrate, wherein said hydrate contains water in the range of from 1.5 to 2.5% w/w and provides a Raman spectrum substantially in accordance with FIG. 3.

6. A crystalline 5-[4-[2-(N-methyl-N-(2-pyridyl)amino)ethoxy]benzyl]thiazolidine-2,4-dione, maleic acid salt, hydrate, wherein said hydrate contains water in the range of from 1.5 to 2.5% w/w and provides a solid state nuclear magnetic resonance spectrum substantially in accordance with FIG. 4.

7. The crystalline hydrate according to claim 1, wherein said hydrate contains water in the range of from 1.5 to 2.0% w/w.

8. The crystalline hydrate according to claim 2, wherein said hydrate contains water in the range of from 1.5 to 2.0% w/w.

9. The crystalline hydrate according to claim 3, wherein said hydrate contains water in the range of from 1.5 to 2.0% w/w.

10. The crystalline hydrate according to claim 4, wherein said hydrate contains water in the range of from 1.5 to 2.0% w/w.

11. The crystalline hydrate according to claim 5, wherein said hydrate contains water in the range of from 1.5 to 2.0% w/w.

12. The crystalline hydrate according to claim 6, wherein said hydrate contains water in the range of from 1.5 to 2.0% w/w.

* * * * *